(12) United States Patent
Ebadollahi et al.

(10) Patent No.: US 10,832,821 B2
(45) Date of Patent: Nov. 10, 2020

(54) DYNAMIC IDENTIFICATION OF THE BIOMARKERS LEVERAGING THE DYNAMICS OF THE BIOMARKER

(71) Applicant: INTERNATIONAL BUSINESS MACHINES CORPORATION, Armonk, NY (US)

(72) Inventors: Shahram Ebadollahi, White Plains, NY (US); Jianying Hu, Bronx, NY (US); Jimeng Sun, White Plains, NY (US); Fei Wang, Ossining, NY (US); Jiayu Zhou, Phoenix, AZ (US)

(73) Assignee: International Business Machines Corporation, Armonk, NY (US)

( * ) Notice: Subject to any disclaimer, the term of this patent is extended or adjusted under 35 U.S.C. 154(b) by 1272 days.

(21) Appl. No.: 13/970,244

(22) Filed: Aug. 19, 2013

(65) Prior Publication Data

US 2014/0236545 A1 Aug. 21, 2014

Related U.S. Application Data

(63) Continuation of application No. 13/770,627, filed on Feb. 19, 2013, now abandoned.

(51) Int. Cl.
*G06G 7/48* (2006.01)
*G16H 50/50* (2018.01)
*G16B 20/00* (2019.01)

(52) U.S. Cl.
CPC .............. *G16H 50/50* (2018.01); *G16B 20/00* (2019.02)

(58) Field of Classification Search
None
See application file for complete search history.

(56) References Cited

U.S. PATENT DOCUMENTS

| 2012/0221075 A1* | 8/2012 | Bentwich | A61B 5/0476 607/45 |
|---|---|---|---|
| 2013/0041015 A1* | 2/2013 | Chatterjee | C12Q 1/48 514/44 A |
| 2014/0236621 A1* | 8/2014 | Six | G01N 33/6893 705/2 |

OTHER PUBLICATIONS

Tibshirani, Robert, et al. "Sparsity and smoothness via the fused lasso." Journal of the Royal Statistical Society: Series B (Statistical Methodology) 67.1 (2005): 91-108.*
Guyon, I., et al. "An Introduction to Variable and Feature Selection" Journal of Machine Learning Research, vol. 3. Mar. 2003. pp. 1157-1182.
Jack Jr., C., et al. "Hypothetical Model of Dynamic Biomarkers of the Alzheimer's Pathological Cascade" Lancet Neurol. Jan. 2010, pp. 1-20.

(Continued)

*Primary Examiner* — Rehana Perveen
*Assistant Examiner* — Nithya J. Moll
(74) *Attorney, Agent, or Firm* — Tutunjian & Bitetto, P.C.; Kristofer Haggerty

(57) ABSTRACT

A system and method for providing a temporally dynamic model parameter include building a model parameter by minimizing a loss function based on patient measurements taken at a plurality of time points. Temporally related values of the model parameter are identified, using a processor, having a same type of patient measurement taken at different time points. At least one value of the model parameter and temporally related values of the at least one value are selected to provide a temporally dynamic model parameter.

15 Claims, 3 Drawing Sheets

(56) References Cited

OTHER PUBLICATIONS

Nesterov, Y. "Gradient Methods for Minimizing Composite Objective Function" Center for Operations Research and Econometrics (CORE) Discussion Paper. Sep. 2007. (32 Pages).
Tibshirani, R. "Regression Shrinkage and Selection Via the Lasso" Journal of the Royal Statistical Society, Series B, vol. 58, No. 1. 1996. (23 Pages).
Yuan, M., et al. "Model Selection and Estimation in Regression With Grouped Variables" Journal of the Royal Statistical Society, Series B, vol. 68, No. 1. Feb. 2006. pp. 49-67.
Zhang, D., et al. "Predicting Future Clinical Changes of MCI Patients Using Longitudinal and Multimodal Biomarkers" PLoS One, vol. 7, No. 3. Mar. 2012. pp. 1-15.

\* cited by examiner

200

┌─────────────────────────────────────────────────────────────┐
│ Minimizing a loss function to build a model parameter based on patient data
│ 202
└─────────────────────────────────────────────────────────────┘
                              ↓
┌─────────────────────────────────────────────────────────────┐
│ Identifying temporal relationships between values of the model parameter of a same type
│ 204
│  ┌───────────────────────────────────────────────────────┐
│  │ Identifying temporal relationships between values of the model parameter of a same biomarker
│  │ 206
│  └───────────────────────────────────────────────────────┘
│  ┌───────────────────────────────────────────────────────┐
│  │ Identifying temporal relationships between values of the model parameter of a same type taken at different points in time
│  │ 208
│  └───────────────────────────────────────────────────────┘
│  ┌───────────────────────────────────────────────────────┐
│  │ Wherein the values of the model parameter of a same type are temporally smooth
│  │ 210
│  └───────────────────────────────────────────────────────┘
└─────────────────────────────────────────────────────────────┘
                              ↓
┌─────────────────────────────────────────────────────────────┐
│ Selecting at least one of the values of the model parameter including temporally related values to provide a temporally dynamic model parameter
│ 212
│  ┌───────────────────────────────────────────────────────┐
│  │ Grouping the at least one of the values of the model parameter including temporally related values to provide temporal spasity
│  │ 214
│  └───────────────────────────────────────────────────────┘
│  ┌───────────────────────────────────────────────────────┐
│  │ Adjusting a grouping of temporally related values to account for a missing value at a point in time
│  │ 216
│  └───────────────────────────────────────────────────────┘
└─────────────────────────────────────────────────────────────┘

FIG. 3

DYNAMIC IDENTIFICATION OF THE BIOMARKERS LEVERAGING THE DYNAMICS OF THE BIOMARKER

RELATED APPLICATION INFORMATION

This application is a Continuation application of copending U.S. patent application Ser. No. 13/770,627 filed on Feb. 19, 2013, incorporated herein by reference in its entirety.

BACKGROUND

Technical Field

The present invention relates to biological markers, and more particularly to the dynamic identification of biomarkers.

Description of the Related Art

Identifying important biomarkers is an important step in the study of many diseases, not only to provide a deeper understanding of the nature of the disease, but also to yield high quality predictive modeling. In longitudinal studies, biomarkers are repeatedly taken from patients at multiple points in time. However, since the cost of obtaining many biomarkers is still very high, there are typically a very limited number of patients that are available in longitudinal studies. In many longitudinal studies, it is believed that a small subset of biomarkers is related to the disease progression and that biomarkers involved at different stages may yield results different (i.e., the dynamics of biomarkers). However, there are few existing feature selection methods that incorporate the temporal information in the study of longitudinal data, and no existing solution can be used to explore the temporal patterns of biomarkers.

SUMMARY

A method for providing a temporally dynamic model parameter includes building a model parameter by minimizing a loss function based on patient measurements taken at a plurality of time points. Temporally related values of the model parameter are identified, using a processor, having a same type of patient measurement taken at different time points. At least one value of the model parameter and temporally related values of the at least one value are selected to provide a temporally dynamic model parameter.

A system for providing a temporally dynamic model parameter includes a formulation module configured to build a model parameter by minimizing a loss function based on patient measurements taken at a plurality of time points and stored on a computer readable storage medium. A relation module is configured to identify temporally related values of the model parameter having a same type of patient measurement taken at different time points. A selection module is configured to select at least one value of the model parameter and temporally related values of the at least one value to provide a temporally dynamic model parameter.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 3 is a block/flow diagram showing a system/method for dynamic biomarker identification, in accordance with one illustrative embodiment.

DETAILED DESCRIPTION OF PREFERRED EMBODIMENTS

Figure 1:
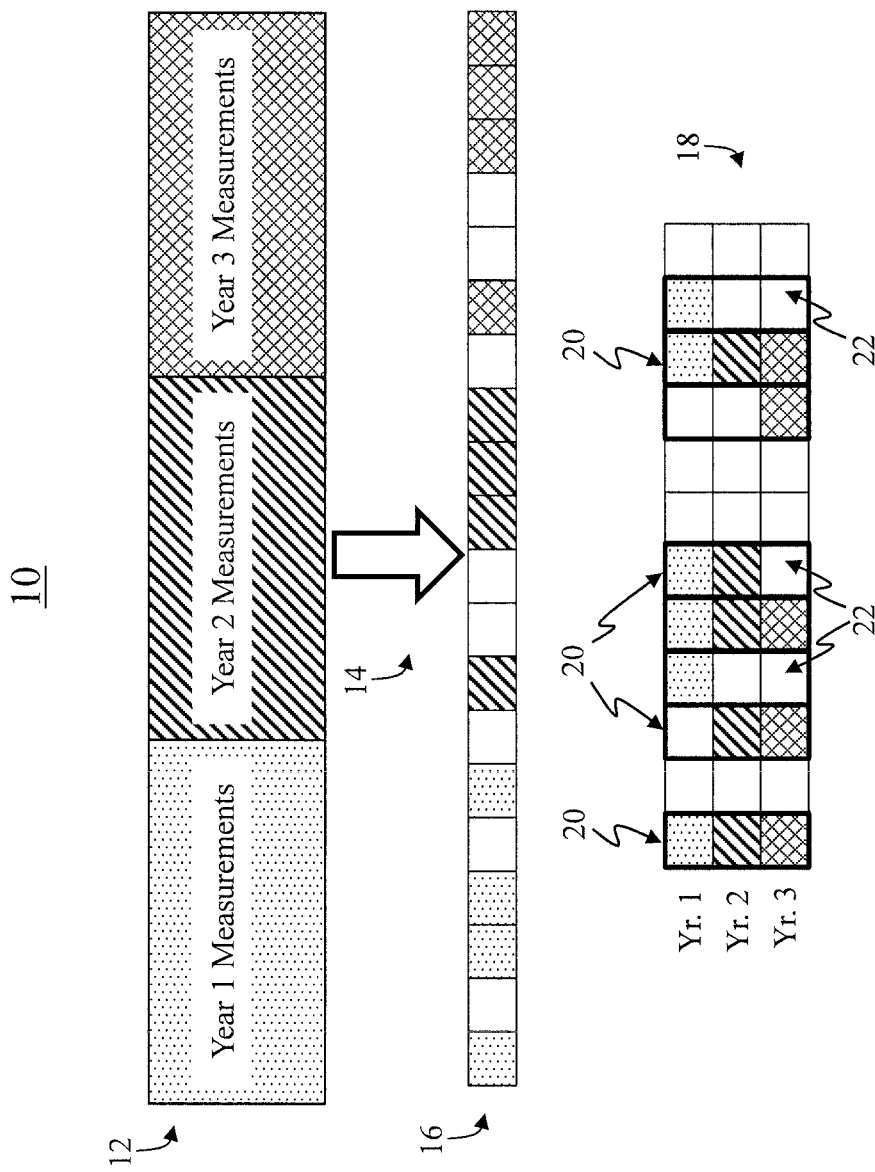
FIG. 1 is an overview of dynamic biomarker identification in accordance with one illustrative embodiment.

In accordance with the present principles, systems and methods for the dynamic identification of biomarkers leveraging the dynamics of the biomarker are provided. An optimization problem is formulated as a minimization of a loss function to build a model parameter based on patient longitudinal data. The model parameter includes a vector having weights representing each biomarker. Temporal relationships between values of the model parameter of the same biomarker taken at different points in time are then identified. Immediate neighboring points of the same biomarker are preferably similar to provide temporal smoothness.

Model parameter values are then selected to provide a temporally dynamic model parameter. Temporal sparsity is provided such that a biomarker that is not selected at one point in time is not likely to be selected at neighboring time points, while a biomarker that is selected at one point in time is likely to be selected at neighboring time points. In one embodiment, the grouping of values of the model parameter may be adjusted to account for missing values for a biomarker at a particular time point. Adjusting the grouping of values of the model parameter may include dropping terms corresponding to the biomarker at the particular time point. The temporally dynamic model parameter may be used for, e.g., patient disease predictions, etc.

Advantageously, the present principles simultaneously build a predictive model and identify dynamic biomarkers, which take into consideration the temporal smoothness.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, an overview of dynamic biomarker identification 10 is illustratively depicted in accordance with one embodiment. Longitudinal studies may be performed for n patients and measurements (e.g., biomarkers) may be repeatedly taken each time period (e.g., year 1, year 2 and year 3) to provide longitudinal data 12. Learning with structured sparsity 14 may be performed on the longitudinal data 12 to provide a temporally dynamic model parameter 16. Learning with structured sparsity 14 accounts for the temporal relationship between biomarkers.

For ease of understanding and illustrative purposes, the vector of the temporally dynamic model parameter 16 is shown to be rearranged as a matrix 18. By stacking the biomarker vector 16 into a matrix 18, the temporal information of the biomarkers can be illustrated in a straight forward way. Advantageously, learning with structured sparsity 14 identifies the temporal sparsity 22 of relevant biomarkers, such that if a biomarker is not selected at one time point, it is not likely to be selected at neighboring time points. Learning with structured sparsity 14 further identifies a small set of biomarkers that are relevant to the prediction task. Learning with structured sparsity 14 will be further explained below.

Figure 2:
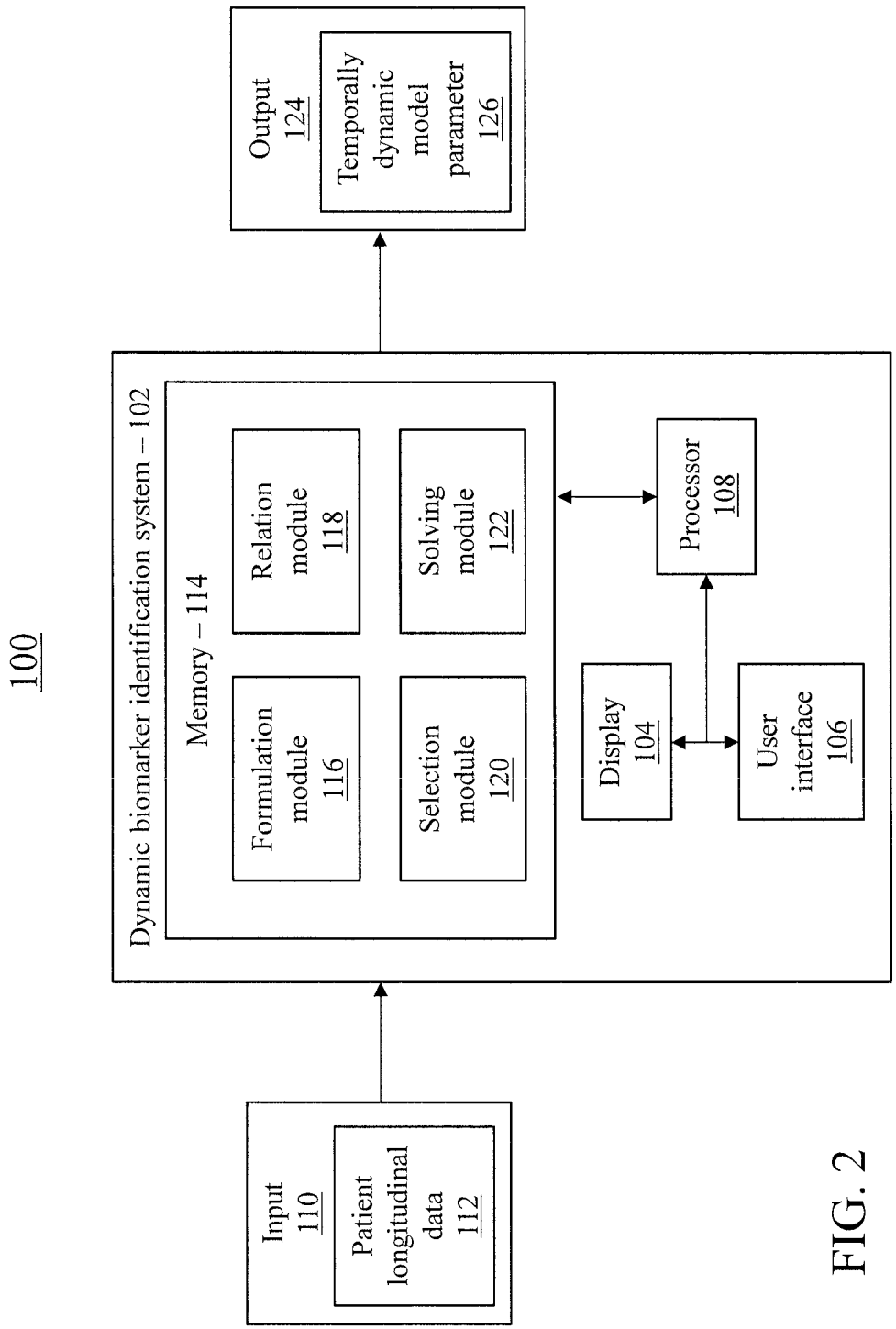
FIG. 2 is a block/flow diagram showing a system/method for dynamic biomarker identification, in accordance with one illustrative embodiment.

Referring now to FIG. 2, a block/flow diagram showing a dynamic biomarker identification system 100 is illustratively depicted in accordance with one embodiment. The dynamic biomarker identification system 100 may include a workstation or system 102. The system 102 preferably includes one or more processors 108 and memory 114 for storing applications, modules and other data.

System 102 may include one or more displays 104 for viewing. The displays 104 may permit a user to interact with the system 102 and its components and functions. This may be further facilitated by a user interface 106, which may include a mouse, joystick, or any other peripheral or control to permit user interaction with the system 102 and/or its devices. It should be understood that the components and functions of the system 102 may be integrated into one or more systems or workstations.

System 102 may receive input 110, which may include patient longitudinal data 112. Patient longitudinal data 112 may include biomarkers from a variety of sources, repeatedly taken from patients at multiple time points (e.g., bimonthly, monthly, semiannually, annually, etc.). The time points may be taken at regular or irregular intervals. Biomarkers are variables that indicate specific features of disease-related pathological changes. Biomarkers may include measurements taken from, e.g., biomedical images (magnetic resonance imaging, positron emission tomography), plasma (proteomics), gene information (microarray), etc.

The patient longitudinal data 112 is provided for n patients enrolled in a longitudinal study over t periods of time (e.g., years). It is assumed that for each year, the same type of d measurements is taken from all patients n. The patient longitudinal data 112 is collectively denoted as $X \in \mathfrak{R}^{n \times (d \cdot t)} = \{X_1, X_2, \ldots, X_t\}$, where $X_i \in \mathfrak{R}^{n \times d}$ is the measurement data for the time point i, and the corresponding output label is given by y.

Memory 114 may include a formulation module 116 configured to build a model parameter w (also referred to as a model or predictive model). An intuitive way for building the model parameter using longitudinal data 112 is to combine all features available for each patient. Typically, the number of measurements is much larger than the number of patients. Therefore, a sparse-inducing regularization may be used to select features when building the model parameter.

In a preferred embodiment, building the model parameter w includes formulating an $l_1$-norm regularization problem, such as, e.g., Lasso (least absolute shrinkage and selection operator), which may receive any kind of data to provide a sparse solution as the model parameter w, which may include a vector. In the vector w, each value represents the weight of a biomarker, where the "selected" biomarkers are the non-zero values in the vector w. Sparsity on the model parameter w refers to the amount of zeroes in w, which indicates that those biomarkers are not selected.

Formulating the regularization problem may include minimizing a loss function L. Mathematically, in one embodiment, to build a model parameter on X is to solve the following optimization problem:

$$\min_w L(w, X, y) + \lambda_1 \|w\|_1 \quad (1)$$

where L is a convex loss function. By minimizing equation (1) with a properly selected $\lambda_1$, sparsity is provided on the model parameter w. The selection of $\lambda_1$ may include cross validation using training data; however, other techniques are also contemplated. The selection of $\lambda_1$ is problem-related and can be calculated using standard optimization analyses. A higher $\lambda_1$ value provides for more sparsity in the model parameter while a lower $\lambda_1$ value provides for more density in the model parameter (i.e., the model parameter w is not likely to have any zeros).

The function L(w, X, y) is a loss function which measures the prediction to provide the output label y. For instance, using linear models, the loss function can be represented as, e.g., $L(w, X, y) = w^T x$, where w is the model parameter. In other embodiments, the loss function can be represented as a squared loss function defined by $L(w, X, y) = \|Xw - y\|_2^{2/n}$, where n is the length of y, or equivalently the number of instances to be predicted. Other embodiments of loss function L are also contemplated.

At each point in time of the longitudinal study, it is assumed that the same types of measurements are used (i.e., the same biomarkers). It is believed that as a disease progresses, biomarkers involved at different stages may be different. It is intuitive to assume that model parameters of the same type of features are related to each other. While the model parameter w may include a vector used to predict the target (i.e., produce the output label y), it does not consider such temporal relatedness among features.

A relation module 118 may be configured to identify temporal relationships between values of the model parameter w of the same biomarker taken at different points in time. A fused Lasso is proposed to capture such relatedness as follows:

$$\min_w L(w, X, y) + \lambda_1 \|w\|_1 + \quad (2)$$
$$\lambda_2 \sum_{i=1}^{d} (\|w_i + w_{d+i}\|_1 + \|w_{d+i} + w_{2d+i}\|_1 + \ldots + \|w_{(t-2)d+i} - w_{(t-1)d+i}\|_1).$$

The fused term can be encoded in a matrix R such that the formulation of equation (2) is denoted as follows:

$$\min_w L(w, X, y) + \lambda_1 \|w\|_1 + \lambda_2 \|Rw\|_1. \quad (3)$$

The term $\lambda_2 \|Rw\|_1$ identifies model values of the same biomarker between immediate points in time such that they are similar to each other. Thus, with a properly selected value of $\lambda_2$ (e.g., by cross validation, etc.), the identified group of model values are more likely to be similar than in equation (1) to thereby provide temporal smoothness. In healthcare analysis, the temporal smoothness indicates that the effect of a biomarker should be similar at nearby time points and, thus, in the predictive model, nearby time points should have similar values.

Besides temporal smoothness, joint feature selection is also incorporated. Selection module 120 is configured to select relevant model values of the same type in the model parameter w taken at different time points. In one embodiment, $l_{2,1}$-norm regularization is incorporated to provide joint feature selection, which gives:

$$\min_w L(w, X, y) + \lambda_1\|w\|_1 + \lambda_2\|Rw\|_1 + \lambda_3\sum_{i=1}^{d}\left(\sqrt{w_i^2 + w_{d+i}^2 + \ldots + w_{(t-1)d+i}^2}\right). \quad (4)$$

The $\lambda_3$ term provides grouped sparsity to select relevant model values of the same biomarker at all time points while irrelevant biomarker model values at all time points are not selected. $\lambda_3$ may be properly selected, e.g., by cross validation, etc. Relevant model values are those that have non-zero weights. In healthcare, relevant features are those that signal the target response.

The proposed formulation of equation (4) gives several kinds of sparsity. The first type of sparsity is similar to Lasso that given "random" sparsity. The second type of sparsity is temporal sparsity, where the selection status of the same type of feature at two immediate time points should be similar (i.e., they tend to be both selected by equation (4) or both not selected). The third type of sparsity is introduced by the $l_{2,1}$, which guarantees that a small subset of features will be selected at all time points.

Solving module 122 is configured to solve the optimization problem of equation (4). In one embodiment, solving module 122 may apply gradient descent or accelerated gradient method (AGM). Other solving techniques are also contemplated.

One important step in using AGM is the computation of a proximal operator associated with the composite of non-smooth penalties, defined as follows:

$$\pi(v) = \operatorname*{argmin}_w \frac{1}{2}\|w - v\|_2^2 + \lambda_1\|w\|_1 + \lambda_2\|Rw\|_1 + \lambda_3\sum_{i=1}^{d}\left(\sqrt{w_i^2 + w_{d+i}^2 + \ldots + w_{(t-1)d+i}^2}\right). \quad (5)$$

The subvector are denoted as $\hat{w}_i=[w_i w_{d+i} \ldots w_{(t-1)d+i}]^T$ and $\hat{v}_i=[v_i v_{d+i} \ldots v_{(t-1)d+i}]^T$. The projection of equation (5) is decoupled for each $\hat{w}_i$ and $\hat{v}_i$:

$$\pi(\hat{v}_i) = \operatorname*{argmin}_{\hat{w}_i} \frac{1}{2}\|\hat{w}_i - \hat{v}_i\|_2^2 + \lambda_1\|\hat{w}_i\|_1 + \lambda_2\|R\hat{w}_i\|_1 + \lambda_3\|\hat{w}_i\|_2. \quad (6)$$

The proximal operator can be decomposed into two steps and solved efficiently. The optimization problem of equation (4) can be solved by applying, e.g., APM (accelerated projected gradient method) with convergence speed $$O\left(\frac{1}{k^2}\right),$$

where k is the iteration number. Solving the optimization problem of equation (4) provides output 124, which may include a temporally dynamic model parameter 126. The model parameter 126 may be used to perform predictions. Pseudocode 1 shows exemplary pseudocode for solving the optimization problem of equation (4), in accordance with one embodiment.

Pseudocode 1: Exemplary Pseudocode for Solving a Dynamic Biomarker Selection Optimization Problem 1: Input: $w_0, \gamma_0 \in \mathfrak{R}$, regularization parameters $\lambda_1, \lambda_2, \lambda_3$ and max iteration number q.
2: Output: w.
3: Set $w_1 = w_0$, $t_{-1} = 0$, and $t_0 = 1$.
4: for i = 1 to q do
5:     Set $\beta_i = (t_{i-2} - 1)/t_{i-1}$
6:     $s_i = w_i + \beta_i(w_i - w_{i-1})$
7:     while (true)
8:       Compute $w^* = \arg\min_w P_{\gamma_i, s_i}(s_i + \nabla_{s_i} L/\gamma_i)$
9:       if $f(w^*) \leq P_{\gamma_i, s_i}(w^*)$ then break the while loop
10:       else set $\gamma_i = \gamma_i \times 2$
11:     end if
12:     end while
13:     Set $w_{i+1} = w^*$ and $\gamma_{i+1} = \gamma_i$
14:     if stopping criterion is satisfied then break the for loop.
15:     Set $t_i = \left(1 + \sqrt{1 + 4t_{i-1}^2}\right)/2$
16: end for
17: Set $w = w_{i+1}$ where $P_{\gamma, s}(w) = f(s) + \langle \nabla_w f(s), w - s \rangle + \frac{\gamma}{2}\|w - s\|_F^2 + \Omega(w, \lambda_1, \lambda_2, \lambda_3)$, and $$\Omega(w, \lambda_1, \lambda_2, \lambda_3) = \lambda_1\|w\|_1 + \lambda_2\|Rw\|_1 + \lambda_3\sum_{i=1}^{d}\left(\sqrt{w_i^2 + w_{d+i}^2 + \ldots + w_{(t-1)d+i}^2}\right), \text{ and}$$

$$\|Rw\|_1 = \sum_{i=1}^{d}(\|w_i + w_{d+i}\|_1 + \|w_{d+i} + w_{2d+i}\|_1 + \ldots + \|w_{(t-2)d+i} - w_{(t-1)d+i}\|_1)$$

In some scenarios, biomarkers measured at different time points may be slightly different. For example, a biomarker may be measured at a first and third time point, but may not be measured at a second time point. By adjusting the grouping of the predictive model w, this situation can be easily handled. In one embodiment, missing features of a biomarker corresponding to the second time point are removed from the optimization problem of equation (4). For example, if the feature corresponding to $w_{d+i}$ is missing, the $w_{d+i}$ term is removed from equation (4) as follows:

$$\min_w L(w, X, y) + \lambda_1\|w\|_1 + \lambda_2\sum_{i=1}^{d}(\|w_i\|_1 + \|w_{2d+i}\|_1 + \ldots + \|w_{(t-2)d+i} - w_{(t-1)d+i}\|_1) + \lambda_3\sum_{i=1}^{d}\left(\sqrt{w_i^2 + \ldots + w_{(t-1)d+i}^2}\right) \quad (7)$$

Referring now to FIG. 3, a method for identifying dynamic biomarkers 200 is illustratively depicted in accordance with one embodiment. In block 202, a model parameter is built by minimizing a loss function based on patient measurements taken at a plurality of time points. Patient measurements may include patient longitudinal data including biomarkers. A sparse inducing regularization is applied to select features from the patient data by minimizing the loss function. A model parameter is provided including a vector representing weights of each biomarker.

In block 204, temporally related values of the model parameter are identified having a same type of patient measurement taken at different time points. The same type of patient measurement may include a same biomarker, in block 206. In block 208, the different time points may include consecutive time points.

In block 210, at least one value of the model parameter and temporally related values of the at least one value are selected to provide a temporally dynamic model parameter. Selecting the at least one of the values of the model parameter may include not selecting irrelevant values of the model parameter including its temporally related values. The at least one value of the model parameter and temporally related values are grouped to provide temporal sparsity. Temporal sparsity provides that a biomarker that is not selected at one point in time is not likely to be selected at neighboring points in time, while a biomarker that is selected at one point in time is likely to be selected at neighboring points in time. In block 212, selecting temporally related values of the at least one value may include selecting all temporally related values of the at least one value. In block 214, a patient condition may be predicted using the temporally dynamic model parameter.

In one embodiment, where features at a particular time point are not present, steps 204 and 212 are adjusted to account for the missing feature. This may include removing terms corresponding to the missing feature from the formulation performed in steps 204 and 212. Other embodiments may be implemented to account for missing features.

The steps of block 202, 204 and 212 may be formulated as an optimization problem to provide the temporally dynamic model parameter. Solving the optimization problem may include applying, e.g., gradient descent or the accelerated gradient method. Other methods are also contemplated.

Having described preferred embodiments of a system and method for dynamic identification of the biomarkers leveraging the dynamics of the biomarker (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer readable storage medium comprising a computer readable program for feature selection with improved learning with structured sparsity, wherein the computer readable program when executed on a computer causes the computer to perform the steps of:
generating a temporally dynamic model parameter including:
inducing random sparsity on a model parameter built from a vector by minimizing a loss function based on patient measurements taken at a plurality of time points in a longitudinal study;
inducing temporal sparsity on the model parameter including a first norm having a fused least absolute shrinkage and selection operator (LASSO) with a fused term encoded in a matrix identifying temporally related values of longitudinal study data having a same type of patient measurement taken at different time points, the temporally related values being identified according to similarity at neighboring points in time for each type of patient measurement, the first norm being weighted by a first coefficient to provide the temporal sparsity;
inducing grouped sparsity on the model parameter, including a second norm including a $l_{2,1}$-norm of the vector, by selecting at least one value relevant to a disease of the longitudinal study data and the temporally related values corresponding to the at least one value, the second norm being weighted with a second coefficient to provide feature selection; and
predicting, using a processor to implement the temporally dynamic model parameter, a future condition of a patient according to data corresponding to a current condition of the patient,
wherein generating the temporally dynamic model parameter includes applying a third norm to the vector to provide the random sparsity, the third norm being weighted by a third coefficient to provide random sparsity, wherein the loss function, together with the applying the third norm, formulates a $l_1$-norm regularization problem.

2. The computer readable storage medium as recited in claim 1, wherein the same type of patient measurement includes the same biomarker.

3. The computer readable storage medium as recited in claim 1, wherein selecting includes selecting all temporally related values of the at least one value.

4. The computer readable storage medium as recited in claim 1, wherein identifying includes removing terms corresponding to a missing value of the model parameter at a time point.

5. The computer readable storage medium as recited in claim 1, wherein the different time points include consecutive time points.

6. The computer readable storage medium as recited in claim 1, further comprising performing $l_{2,1}$-norm regularization to provide joint feature selection, as part of equation:

$$\min_{w} L(w, X, y) + \lambda_1 \|w\|_1 + \lambda_2 \|Rw\|_1 + \lambda_3 \sum_{i=1}^{d} \left( \sqrt{w_i^2 + w_{d+i}^2 + \ldots + w_{(t-1)d+i}^2} \right)$$

where L(w, X, y) is a loss function, $\lambda_2$ is a coefficient determined to provide temporal smoothness, R is a matrix of fused terms, w is the model parameter, $\lambda_3$ provides grouped sparsity to select relevant model values of a same biomarker at all time points while irrelevant biomarker model values at all time points are not selected, "i" is an index for the different time points, "d" is an index of measurements taken during the longitudinal study, and "t" is the time period over which the longitudinal study was conducted.

7. A system for providing a temporally dynamic model parameter with improved learning with structured sparsity, comprising:
a memory configured to generate a temporally dynamic model parameter, the memory including:
a formulation module configured to induce random sparsity on model parameter built from a vector by minimizing a loss function based on patient measurements taken at a plurality of time points in a longitudinal study and stored on a computer readable storage medium;
a relation module configured to induce temporal sparsity on the model parameter by applying a first norm including a fused least absolute shrinkage and selection operator (LASSO) with a fused term encoded in a matrix identifying temporally related values of longitudinal study data having a same type of patient measurement taken at different time points, the temporally related values being identified according to similarity at neighboring points in time for each type of patient measurement, the first norm being weighted by a first coefficient to provide the temporal sparsity;

a selection module configured to induce grouped sparsity on the model parameter by applying a second norm including an $l_{1,2}$-norm of the vector, and selecting at least one value relevant to a disease of the longitudinal study data and the temporally related values of the at least one value to provide a temporally dynamic model parameter, the second norm being weighted with a second coefficient to provide feature selection; and a solving module including a processor configured to predict, with the temporally dynamic model parameter, a future condition of a patient according to data corresponding to a current condition of the patient, wherein the formulation module is further configured to formulate a $l_1$-norm regularization problem by combining the minimized loss function with applying a third norm to the vector, the third norm being weighted by a third coefficient to provide random sparsity, wherein the loss function, together with the applying the third norm, formulates a $l_1$-norm regularization problem.

8. The system as recited in claim 7, wherein the same type of patient measurement includes a same biomarker.

9. The system as recited in claim 7, wherein the selection module is further configured to select all temporally related values of the at least one value.

10. The system as recited in claim 7, wherein the relation module is further configured to remove terms corresponding to a missing value of the model parameter at a time point.

11. The system as recited in claim 7, wherein the different time points include consecutive time points.

12. The system as recited in claim 7, wherein patient measurements include patient longitudinal data.

13. The system as recited in claim 7, wherein the selection module is further configured to perform $l_{2,1}$-norm regularization to provide joint feature selection, as part of equation:

$$\min_w L(w, X, y) + \lambda_1 \|w\|_1 + \lambda_2 \|Rw\|_1 + \lambda_3 \sum_{i=1}^{d} \left( \sqrt{w_i^2 + w_{d+i}^2 + \ldots + w_{(t-1)d+i}^2} \right)$$

where $L(w, X, y)$ is a loss function, $\lambda_2$ is a coefficient determined to provide temporal smoothness, R is a matrix of fused terms, w is the model parameter, $\lambda_3$ provides grouped sparsity to select relevant model values of a same biomarker at all time points while irrelevant biomarker model values at all time points are not selected, "i" is an index for the different time points, "d" is an index of measurements taken during the longitudinal study, and "t" is the time period over which the longitudinal study was conducted.

14. The system as recited in claim 7, wherein;
the first norm is weighted by a first coefficient to provide temporal sparsity;
the second norm is weighted by a second coefficient to provide feature selection; and
the third norm is weighted by a third coefficient to provide random sparsity.

15. A method for predicting disease progression with a model parameter using feature selection with improved learning with structured sparsity, the method comprising:
measuring values for a selected set of biomarkers at multiple time points for each of a plurality of study participants;
inducing random sparsity on the model parameter by minimizing a loss function based on the selected set of biomarkers;
identifying at each point in time, from the selected set of biomarkers, temporally smooth values similar to values of corresponding biomarkers at neighboring points in time using a first norm including a fused least absolute shrinkage and selection operator (LASSO) with a fused term encoded in a matrix, the first norm being weighted by a first coefficient to provide the temporal sparsity;
identifying predictive features from the temporally smooth values that correspond to a target response of a disease by applying a second norm including a $l_{1,2}$-norm of selected set of biomarkers, the second norm being weighted with a second coefficient to provide feature selection;
correlating the predictive features to disease progression for the disease;
predicting a future condition of a patient relative to the disease according to patient biomarkers; and
displaying the future condition via a display to a user, wherein
inducing random sparsity includes applying a third norm to the selected set of biomarkers, the third norm being weighted by a third coefficient to provide random sparsity, wherein the loss function, together with the applying the third norm, formulates a $l_1$-norm regularization problem.

* * * * *